United States Patent [19]

Haubennestel et al.

[11] Patent Number: 4,696,761
[45] Date of Patent: Sep. 29, 1987

[54] DE-FOAMER AND PROCESSES FOR ITS PRODUCTION

[75] Inventors: Karlheinz Haubennestel, Wesel; Daniela Breil, Hamminkeln; Alfred Bubat, Wesel-Bislich; Werner Spratte, Wesel-Flüren, all of Fed. Rep. of Germany

[73] Assignee: Byk-Chemie GmbH, Wesel, Fed. Rep. of Germany

[21] Appl. No.: 860,686

[22] Filed: May 2, 1986

Related U.S. Application Data

[63] Continuation of Ser. No. 558,153, Dec. 5, 1983.

[30] Foreign Application Priority Data

Dec. 8, 1982 [DE] Fed. Rep. of Germany ....... 3245482

[51] Int. Cl.$^4$ .......... B01D 17/04; B01D 19/04
[52] U.S. Cl. ................ 252/358; 252/321
[58] Field of Search ................ 252/321, 358

[56] References Cited

U.S. PATENT DOCUMENTS

| | | | |
|---|---|---|---|
| 2,469,450 | 5/1949 | Bird et al. | 252/321 |
| 2,580,922 | 1/1952 | Jacoby | 252/321 |
| 3,243,372 | 3/1966 | Dreher | 564/56 X |
| 3,522,304 | 7/1970 | Vogt | 564/32 X |
| 3,751,370 | 8/1973 | Stimberg et al. | 252/321 X |
| 3,923,683 | 12/1975 | Michalski et al. | 252/321 |
| 3,990,905 | 11/1976 | Wachala | 252/321 X |
| 4,094,812 | 6/1978 | Heyden et al. | 252/321 |
| 4,104,287 | 8/1978 | Fischer et al. | 564/56 X |
| 4,107,073 | 8/1978 | Maciaszek | 252/321 |
| 4,110,309 | 8/1978 | Schulze et al. | 564/56 X |
| 4,317,819 | 3/1982 | Clitherow et al. | 564/56 X |

FOREIGN PATENT DOCUMENTS 925940  5/1982  U.S.S.R. ................ 564/56

Primary Examiner—John F. Terapane
Assistant Examiner—Catherine S. Kilby
Attorney, Agent, or Firm—Michael J. Striker

[57] ABSTRACT

To produce a de-foamer, mono- and/or poly-functional isocyanate is reacted with mono- and/or polyfunctional amines, preferably in equivalent ratio 0.5:1 up to 1:0.2, in an organic carrier media, to form urea sols at temperatures which lie below the melting temperature of the resulting urea, the organic carrier medium not being a true solvent for the urea. The prepared ureas are represented by the general Formula 1:

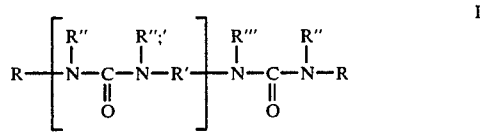

wherein r = $C_4$–$C_{30}$-alkyl; R' = $C_2$–$C_{12}$-alkylene, phenylene or naphthalene with or without substitution by one or more $C_1$–$C_9$-alkyl groups, or cycloalkylene; R'—H or $CH_3$; R''—H or methyl; and x=0 to 1, and are prepared by reacting isocyanates with amines in organic carrier media to form ureas of Formula 1, at temperatures lying below the melting temperature of the resulting urea, the organic carrier media not being true solvents for the urea.

8 Claims, No Drawings

DE-FOAMER AND PROCESSES FOR ITS PRODUCTION

This is a continuation of application Ser. No. 558,153, filed Dec. 5, 1983.

BACKGROUND OF THE INVENTION

It has been known to control foaming particularly in aqueous systems, by means of anti-foaming agents. In many industrial processes, which employ aqueous solutions or suspensions, the foaming is one of the most important problems. A number of suggestions have been made in the past, in order to avoid or to destroy such foam. Such suggestions describe the employment of silicon oil or silicon oil emulsions, dispersions of hydrophobic silica, compounds with fatty acid amides, long-chain alcohols, hydrophobic polyglycolethers, aluminum- and magnesium-stearates as well as mixtures of these products with one another.

All these suggestions aim at a solution to the problem in the most different product-technical areas, such as e.g. waste water treatment, paper production, sugar beet washing, emulsion polymerizations, as well as the preparation of dispersion dyes, where the using foam restrains not only the production, but also causes many problems to the user with regard to the appearance of painted surfaces and poor corrosion protection due to occluded bubbles.

The production of de-foaming compositions previously was technically costly and involved high energy costs as well as very complex de-foaming formulations.

DESCRIPTION OF PRIOR TECHNIQUES

U.S. Pat. Nos. 3,677,963 and 3,652,453, for example, describe processes in which fatty acid amides employed in known amounts are brought into a finely dispersed form by means of a shock-like cooling process, which operation should be superior in contrast to dispersions customarily produced through slow cooling.

The quick settling of the dispersed solid bodies from the carrier medium is a disadvantage with all the previous processes. This occurs particularly strongly with hydrophobic silicic acids. A further disadvantage of these processes is that, required by high tensile concentrations in the foaming medium, a wetting of the hydrophobic particles ensues, and therewith a loss of effectiveness upon storage of the medium used with de-foamers. This is particularly noticeable upon longer storage and higher temperatures.

OBJECTS AND SUMMARY OF THE INVENTION

It is therefore an object according to the present invention to develop as an universal as possible a de-foamer, which offers a high measure of certainty with regard to de-foaming of the most different aqueous systems, with low technical expenditure. Other objects will be evident from a reading of the specification.

In an unexpected manner it has been shown that ureas, which are produced in situ in an organic carrier medium at relatively low temperatures, display excellent de-foaming characteristics for aqueous media.

Ureas with de-foaming characteristics are obtained by mixing together, preferably equivalent amounts of isocyanates and amines in the appropriate organic carrier medium at temperatures below the melting point of the reaction product. If, however, these ureas are heated above their melting point, or are manufactured at temperatures above their melting point, then they possess still only an insignificant de-foaming activity. The de-foamer according to the present invention is a reaction product of mono- and/or polyfunctional isocyantates with mono- and/or polyfunctional amines in an NCO/amine-equivalent ratio preferably between 0.5:1 and 1:0.2, which are reacted to form urea sols at temperatures lying below the melting temperature of the resulting urea, in an organic carrier medium, the organic carrier medium not being a true solvent for the urea. Ureas of the Formula 1 are produced:

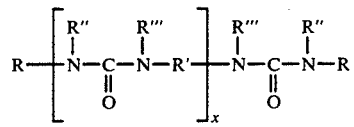

wherein
$R = C_4-C_{30}$-alkyl;
$R' = C_2-C_{12}$-alkylene, phenylene or naphthalene, with or without substitution by $C_1-C_9$-alkyl, or cycloalkylene;
$R'' = H$ or $CH_3$;
$R''' = H$ or methyl; and
$x = 0$ to $1$.

It is essential to the present invention that the reaction of these components occur in situ, so that the formed urea will be produced in monodispersed or in micellar structures in the organic carrier medium.

Particularly preferred are reaction products of stearyl isocyanate and/or palmityl isocyanate with oleylamine, stearylamine and/or distearylamine. Moreover, suitable reaction products are those from mixtures of stearylamine with hexamethylenediamine and toluylenediisocyanate. To a similar extent, known polyamines, such as e.g. ethylenediamine, propanediamine, butanediamine, hexanediamine, 1,12-dodecanediamine, 4,4'-diaminodiphenylmethane, 3,3'-dimethyl-4,4'-diaminodiphenylmethane, p-xylylenediamine, isophorondiamine and hydrazine can be employed, as well as their mixtures with one another.

According to the present invention there are included also reaction products of monoamines with polyisocyanates, particularly with the easily accessible diisocyanates, such as 2,4- and 2,6-toluylenediisocyanate, hexamethylenediisocyanate, naphthylenediisocyanate and/or 4,4'-diaminodiphenylmethanediisocyanate. Also suitable as monoisocyanate are all isocyanates obtained by phosgenization reactions from known monoamines, particularly however 2-ethylhexylisocyanate, isotridecylisocyanate, palmityl-stearylisocyanate, as well as any $C_{18}-C_{24}$-alkylisocyanate.

The ureas effective as de-foamer are manufactured according to the present invention in an organic carrier medium. The concentration of urea in the carrier medium is limited, as required by the resulting viscosities, and lies between 0.2% by weight and 50% by weight, preferably however between 1.0% by weight and 5.0% by weight, relative to the organic carrier medium. This organic carrier medium can in most cases be a paraffin-basic mineral oil but also naphthene-basic and aromatic mineral oils, as well as mixtures of these with one another. From case to case it must also be decided whether or not mixtures of mineral and native oils, such as e.g. soybean oil or sunflower oil, can be advantageous. This depends in great extent on the later field of use of the de-foamer as well as on the type of urea. Moreover, low boiling mineral spirits, xylene, toluene, medicinal paraffin oils, esters of long-chain fatty acids, such as isobutylstearates and isooctylstearates, polyalkyleneglycols and combinations of these products with mineral oils can be employed.

Upon application of the de-foamer into the dispersion dye, with high portion of fillers, an addition of polypropyleneglycol can be advantageous. The de-foamer according to the present invention can additionally contain emulsifiers, which facilitates their incorporation into aqueous systems or makes it possible, to produce from the de-foamer a stock emulsion, which is added to the systems to be de-foamed. In these cases the de-foamer is thereby characterized in that 1–10% by weight non-ionogenic emulsifier, which displays an HLB value from 4 up to 18, is added to the organic carrier media. By HOB value is to be understood a number which characterizes the hydrophilia or hydrophobia of an emulsifier (E. C. Griffin "Classification of Surface Active Agents by HLB", J. Soc. Cosmetics Chemists 1, 311 (1950)). There can be employed emulsifiers of a single type or mixtures of emulsifiers. Examples of such emulsifiers include e.g. fatty alcohols—ethoxilate, nonylphenolethoxilate, sorbitane ester, fatty acid ethoxilate.

For uses where organic carrier media are troublesome, emulsions of de-foamer according to the present invention are expediently employed. These emulsions are formulated according to known techniques as oil-in-water or water-in-oil emulsions.

The novel features which are considered as characteristic for the present invention are set forth in particular in the appended claims. The invention itself, however, both as to its product and process aspects, together with additional objects and advantages thereof, will be best understood from the following description of specific embodiments.

DESCRIPTION OF THE PREFERRED EMBODIMENTS

The following Examples 1–10 and 12–16 describe the production of de-foamer according to the present invention and also give the production of several corresponding de-foamers as comparison Examples.

EXAMPLE 1

280 g of a paraffin-basic mineral oil (viscosity 66.5/SUS/37.8° C.) are heated in a stirred vessel to about 40° C. and then mixed with 1.14 g m-xylenediamine and stirred for a sufficient period until the amine is completely dissolved. After the addition of 4.86 g octadecylisocyanate, the reaction period amounted to 30 minutes.

EXAMPLE 2

273 g of a technical white oil (viscosity 89.5/SUS/37.8° C.) are heated in a stirred vessel to 35° C., and then mixed with 1.82 g octylamine and stirred for a longer period until the amine is completely dissolved. After the addition of 1.18 g 1,6-hexamethylenediisocyanate, the after-reaction period amounted to 30 minutes. Subsequently, 3 g of a hydrophobic silicic acid (oil number 180 g/100 g) are dispersed into the reaction mixture.

EXAMPLE 3

In a stirred vessel are provided 280.5 g of a naphthene-basic mineral oil (viscosity 152/SUS/37.8° C.), which are then heated to 50° C. and mixed with 1.26 g oleylamine. The mixture is then stirred until the amine is completely dissolved. After the addition of 1.74 g octadecylisocyanate, the after-reaction period amounted to 30 minutes at 50° C. Subsequently are added 1.5 g polydimethylsiloxane (viscosity 200 cSt/25° C.), and the reaction mixture is homogenized and cooled down to 30° C.

EXAMPLE 4

120 g of a naphthene-basic mineral oil (viscosity 151/SUS/37.8° C.) are heated in a stirred vessel to 50° C., then with 3.33 g octadecylamine, and stirred for a period of time until the amine is complete dissolved. After the addition of 1.17 g xylenediisocyanate, the after-reaction period amounted to 30 minutes, whereby the temperature rose from 50° C. to 55° C. Subsequently there are successively added 160.5 g polypropyleneglycol (molecular weight about 1,000) and 15 g sorbitane monooleate, followed by homogenization and cooling down to about 30° C.

EXAMPLE 5

In a stirred vessel, 105 g of a paraffin-basic mineral oil (viscosity 125/SUS/37° C.) are mixed with 0.63 g diethylene triamine at 25° C., which are then stirred until the amine is completely dissolved. After the addition of 5.37 g octadecylisocyanate, the after-reaction period amounted to 30 minutes, whereby the temperature rose to 32° C. Subsequently are added, successively, 174 g of a white mineral spirit (boiling range 150°–195° C.), 9 g of a hydrophobic silicic acid (oil number 200 g/100 g) and 9 g of a nonylphenolethoxylate (nonylphenol+6EO), followed by homogenization.

EXAMPLE 6

285 g isododecane are heated in a stirred vessel to 80° C., and mixed with 4.53 g octadecylamine. The mixture is stirred until the entire amine is dissolved. After the addition of 1.47 g 4-methyl-m-phenylenediisocyanate, the after-reaction period amounted to 15 minutes. After the addition of 9 g of a nonylphenylethoxylate (nonylphenyl+7EO), the reaction mixture is homogenized and cooled down to about 30° C.

EXAMPLE 7

In a stirred vessel are mixed 285 g of a refined sunflower oil at 25° C. with 2.55 g octadecylisocyanate and 2.16 g 1,6-hexamethylenediisocyanate. The mixture is stirred until the isocyanate is completely dissolved. After the addition of 1.29 g 1,3-diaminopropane, the after-reaction period amounted to 15 minutes. Subsequently are added 9 g sorbitane monooleate, followed by a further 15 minutes homogenization.

EXAMPLE 8

150 g of a naphthene-basic mineral oil (viscosity 210/SUS/37.8° C.) are heated in a stirred vessel to 60° C. and mixed with 0.54 g hexamethylenediamine. The mixture is stirred until the entire amine is dissolved. After the addition of 1.46 g octadecylisocyanate, the after-reaction period amounted to 30 minutes. Subsequently are added successively 9 g of a nonylphenylethoxylate (nonylphenyl+7EO), 9 g of a hydrophobic silicic acid (oil number 180 g/190 g) and 0.6 g of a polydimethylsiloxane (viscosity 100 cSt/25° C.), followed by homogenization and cooling down to 30° C.

EXAMPLE 9

In a stirred vessel, 956.25 g of a paraffin-basic mineral oil (viscosity 210/SUS/37.8° C.) are heated up to 60° C. and mixed with 1.8 g hexamethylenediamine, stirred until a complete dissolution of the amine, and then reacted with 8.2 g octadecylisocyanate. The after-reaction lasted 15 minutes. Subsequently were added 20 g of a polyoxyethylene-sorbite-hexane-oleate (HOB10.2) and 5 g of tall oil fatty acid, followed by homogenization.

In a second stirrer vessel, 250 g de-mineralized water is provided and heated up to 60° C., after which under strong stirring the urea suspension is slowly added. The final emulsification follows through the use of a colloid mill at 60° C. After cooling down to 30° C. under stirring, the emulsion is de-aerated by means of a vacuum.

EXAMPLE 10

197.5 g of a technical paraffin oil (viscosity 89. 5 SUS/37.8° C.) are mixed in a stirred vessel with 1.9 g xylenediamine at 25° C., and stirred until complete dissolution amine. After the addition of 8.1 g octadecylisocyanate, the after-reaction took 30 minutes. Subsequently, 15 g sorbitane monooleate are added, and, under strong stirring, 275 g of demineralized water are slowly added. After the addition of 2.5 g 37% aqueous formaldehyde solution, the final emulsification followed by means of a colloidal mill. The prepared emulsion was then de-aerated by means of a vacuum under stirring.

EXAMPLE 11

In a stirred vessel, 134 g of a technical paraffin oil (viscosity 89.5/SUS/37.8° C.) are heated to 220° C. and mixed with 1.82 g octylamine. The mixture is slowly stirred until the amine is complete dissolved. After the addition of 1.18 g 1,6-hexamethylenediisocyanate, and an after-reaction period of 30 minutes, the reaction mixture is dripped into a second stirred vessel, under intense stirring and cooling, containing 143 g of a technical paraffin oil cooled down to 20° C. Subsequently, 3 g of a hydrophobic silicic acid (oil number 180 g/100 g) and 5 g of a nonylphenylethoxylene (nonylphenyl+6EO) are added using high shear forces.

The results shown in Tables I and II prove that a later cooling of the already formed urea derivatives does not produce particularly effective defoamers.

EXAMPLE 12

232.5 g of a paraffin-basic mineral oil (viscosity 66.5/SUS/37.8° C.) are heated in a stirred vessel to 30° C., mixed with 0.55 g diaminopropane, and stirred until the amine is completely dissolved. After the addition of 4.45 g octadecylisocyanate, the after-reaction period amounted to 30 minutes. Subsequently, 12,5 g sorbitane monooleate are added, followed by stirring for a further 15 minutes (melting point of the reaction product from diaminopropane and octadecylisocyanate: 105° C.).

EXAMPLE 13

In a stirred vessel, 232.5 g of a naphthene-basic mineral oil (viscosity 152/SUS/37.8° C.) are provided, heated to 40° C. and mixed with 0.98 g 1,4-diaminobutane. The mixture is stirred until the amine is completely dissolved. After the addition of 9.80 g octadecylisocyanate, the after-reaction period amounted to 30 minutes. Subsequently, 7.5 g of a nonylphenylethoxylate (nonylphenyl+6EO) and 2.5 g of a hydrophobic silicic acid (oil number 180 g/100 g) are added using high shear forces.

EXAMPLE 14

236.3 g of a technical paraffin oil (viscosity 89.5/SUS/37.8° C.) are heated in a stirred vessel to 35° C., and mixed with 3.16 g 1,12-diaminododecane. The mixture is stirred until the amine is completely dissolved. After the addition of 4.68 g octadecylisocyanate, the after-reaction period amounted to 30 minutes. Subsequently, 7.5 g sorbitane monooleate are added and the mixture is stirred for another 15 minutes.

EXAMPLE 15

In a stirred vessel, 225 g of a napthene-basic mineral oil (viscosity 85/SUS/37.8° C.) are mixed with 0.4 g hydrazine hydrate, and under intense stirring 4.6 g octadecylisocyanate are added. The after-reaction period amounted to 3 hours. Subsequently 12.5 g of a nonylphenylethoxylate (nonphenyl+7EO) and 7.5 g of a hydrophobic silicic acid (oil number 180 g/100 g) are added using high shear forces.

EXAMPLE 16

230 g isododecane are heated in a stirred vessel to 60° C., mixed with 5.73 g octadecylamine, and stirred for a period until the amine is completely dissolved. After the addition of 1.78 g 1,6-hexamethylenediisocyanate, the after-reaction period amounted to 45 minutes. After the addition of 12.5 g sorbitane monooleate, the reaction mixture is homogenized and cooled down to 30° C.

COMPARATIVE EXAMPLES

Comparative products A, B and C are de-foaming preparations prepared according to U.S. Pat. No. 4,021,365 (Examples 1, 2 and 3).

The comparative products D and E are commercially available de-foamers based upon mineral oils, which are produced according to the following technique:

Comparative Product D

In a stirred vessel, 217.5 g of napthene-basic mineral oil (viscosity 152 SUS/38° C.) are provided, and by means of high shear force, 25 g of a hydrophobic silicic acid and 7.5 g of an emulsifier (nonylphenyl+7EO) are added.

Comparative Product E

In a stirrer vessel 232.5 g of a naphthene-basic mineral oil (viscosity 215 SUS/38° C.) are provided, and succesively are added, under stirring, 5 g of a hydrophobic silicic acid, 7.5 g magnesium stearate and 7.5 g of an emulsifier (nonylphenyl+7EO). After heating up to 100°–105° C., the temperature is maintained for 1 hour. Subsequently, the mixture is allowed to cool down to approximately 40° C. under stirring.

| TECHNICAL USE TEST (T = statements of parts by weight) | |
|---|---|
| 1. Latex paint - interior | |
| vinylacetate/vinylester-copolymerizate dispersion (50%) | 121.5 T |
| sodium polyphosphate | 5.0 T |

-continued
TECHNICAL USE TEST
(T = statements of parts by weight)

| | |
|---|---|
| ammonium polyacrylate | 1.5 T |
| ammonia | 1.5 T |
| preservation agent | 0.5 T |
| white mineral spirit | 6.0 T |
| dipropylene glycol methylether | 2.0 T |
| titanium dioxide | 61.0 T |
| calcium carbonate | 207.0 T |
| talc | 22.0 T |
| thickener | 2.5 T |
| water | 68.0 T |
| de-foamer | 1.0 T |
| 2. Gloss latex paint | |
| acryl-polymer dispersion (50%) | 265.5 T |
| titanium dioxide | 125.0 T |
| propylene glycol | 34.5 T |
| ethyl cellusolve | 9.2 T |
| dipropylene glycol methylether | 7.5 T |
| hydroxyethyl cellulose (2%) in water | 50.0 T |
| sodium polyacrylate | 4.0 T |
| preservation agent | 0.5 T |
| water | 34.5 T |
| de-foamer | 2.5 T |
| 3. Semi-gloss latex paint | |
| styrene/acrylate dispersion (50%) | 358.4 T |
| titanium dioxide | 143.2 T |
| calcium carbonate | 143.2 T |
| hydroxyethyl cellulose (2%) in water | 70.0 T |
| butyl cellosolve | 21.6 T |
| highly ethoxylated, partially unsaturated fatty alcohol | 18.0 T |
| sodium polyphosphate | 3.8 T |
| ammonium polyacrylate | 0.8 T |
| preservation agent | 2.4 T |
| white mineral spirit | 1.8 T |
| ammonia | 0.4 T |
| de-foamer | 2.4 T |
| water | 32.9 T |

The following technical use tests were performed with the dispersion paints listed above:

(a) Test on the prepared paint

Subsequent to the production of the dispersion paint and after a heat storage of seven days at 50° C., 80 parts of the paint are blended with 20 parts water and stirred for 1 minute at 2000 rpm using a dissolver (dispersion disc of 40 mm diameter). Subsequently, the weight of 50 ml of this mixture is determined. The higher the weight of the sample, the lower will be its air content, and the better will be the effect of the de-foamer.

(b) Test using the foam roll (500 $cm^2$ on the penetration contrast board of hard PVC)

50 g dispersion paint is applied onto the penetration contrast board and uniformly distributed with a foam roll so that 12.5 g of wet paint (=250 $g/m^2$) remain. By using the foam roll (6 cm wide; 7 cm diameter) composed of open-pore polyurethane foam, not only will the volume of foam bubbles enclosed in the paint be determined, but additionally the air which—similarly to an application by brush—gets worked into the paint. After drying, the paint is subjected to a visual assessment of air inclusion (bubble formation) and pinholes according to the following comparison scale:

1 = no air included;
2 = variable air included;
3 = no air included;
4 = moderate air inclusion;
5 = strong air occlusion;
6 = very strong air occlusion.

The results are summarized in the following Tables I and II and clearly demonstrate the superiority of the agents according to the present invention. Example II shows the clear loss of effectiveness compared to the similarly formulated Example 2, when the urea is produced from the melt.

TABLE I

Test of antifoaming agents (immediately after manufacturing of the paint)

| | Latex paint - interior | | gloss latex paint | | semi-gloss latex paint | |
|---|---|---|---|---|---|---|
| | air inclusion (% by wt.) | application on contrast board | air inclusion (% by wt.) | application on contrast board | air inclusion (% by wt.) | application on contrast board |
| Comparative product A | 15.5 | 4 | 16.3 | 4 | 20.4 | 4 |
| Comparative product B | 13.2 | 3 | 15.1 | 3 | 18.9 | 3 |
| Comparative product C | 14.6 | 3 | 15.9 | 3 | 19.1 | 3 |
| Comparative product D | 12.9 | 2–3 | 14.8 | 3 | 18.5 | 2–3 |
| Comparative product E | 13.7 | 3–4 | 15.6 | 3–4 | 19.3 | 4 |
| Example 1 | 13.5 | 3 | 14.6 | 3 | 19.5 | 3 |
| Example 2 | 12.8 | 3–4 | 15.3 | 3–4 | 18.1 | 3 |
| Example 3 | 14.1 | 3 | 15.9 | 3–4 | 19.8 | 3–4 |
| Example 4 | 10.7 | 1–2 | 10.1 | 2 | 12.5 | 2 |
| Example 5 | 9.9 | 1 | 9.6 | 1 | 9.8 | 1 |
| Example 6 | 10.2 | 2 | 9.2 | 1 | 10.1 | 1 |
| Example 7 | 11.1 | 2 | 10.5 | 2 | 9.4 | 1 |
| Example 8 | 10.4 | 2 | 9.8 | 2 | 12.3 | 2 |
| Example 9 | 12.5 | 2 | 11.1 | 2–3 | 13.5 | 2 |
| Example 10 | 12.8 | 2–3 | 10.6 | 2–3 | 11.2 | 1–2 |
| Example 11 | 25.3 | 5 | 22.1 | 5 | 25.7 | 5–6 |

TABLE II

Test of antifoaming agents (after 7 days heat storage at 50° C.)

| | Latex paint - interior | | gloss latex - paint | | semi gloss - latex paint | |
|---|---|---|---|---|---|---|
| | air inclusion (% by wt.) | application on contrast board | air inclusion (% by wt.) | application on contrast board | air inclusion (% by wt.) | application on contrast board |
| Comparative product A | 25.1 | 5 | 28.2 | 5 | 28.9 | 5 |
| Comparative product B | 21.4 | 4–5 | 26.5 | 5 | 30.1 | 5 |
| Comparative product C | 23.8 | 5 | 24.8 | 4–5 | 29.5 | 4–5 |
| Comparative product D | 24.5 | 5 | 26.3 | 5 | 30.6 | 5 |

TABLE II-continued

Test of antifoaming agents (after 7 days heat storage at 50° C.)

| | Latex paint - interior | | gloss latex - paint | | semi gloss - latex paint | |
|---|---|---|---|---|---|---|
| | air inclusion (% by wt.) | application on contrast board | air inclusion (% by wt.) | application on contrast board | air inclusion (% by wt.) | application on contrast board |
| Comparative product E | 22.3 | 5 | 27.6 | 5–6 | 31.4 | 5–6 |
| Example 1 | 18.6 | 3–4 | 22.7 | 3–4 | 27.1 | 3–4 |
| Example 2 | 20.3 | 4 | 23.6 | 4 | 25.8 | 3–4 |
| Example 3 | 20.1 | 3–4 | 23.1 | 4 | 28.3 | 4 |
| Example 4 | 11.6 | 1–2 | 10.9 | 2 | 14.1 | 2–3 |
| Example 5 | 10.3 | 1 | 10.3 | 1–2 | 12.0 | 1–2 |
| Example 6 | 10.5 | 2 | 9.9 | 1 | 11.3 | 1 |
| Example 7 | 11.9 | 2 | 10.8 | 2 | 10.6 | 1–2 |
| Example 8 | 12.1 | 2–3 | 10.2 | 2–3 | 13.7 | 2–3 |
| Example 9 | 12.8 | 2 | 12.8 | 3 | 15.2 | 2–3 |
| Example 10 | 13.2 | 2–3 | 11.9 | 3 | 12.4 | 2 |
| Example 11 | 27.4 | 6 | 29.5 | 5 | 30.8 | 5–6 |

USE OF THE DE-FOAMER ACCORDING TO THE INVENTION FOR THE EMULSION POLYMERISATION

A 500 ml three-necked flask equipped with stirrer, dripping funnel, reflux condenser, thermometer and nitrogen conduit is evacuated and then filled with nitrogen. Thereafter are provided 5 g polyvinyl alcohol, which is dissolved in 100 ml distilled water, under stirring, at 60° C. Subsequently are added yet 2.2 g ethoxylated nonylphenol, as well as 0.4 g ammonium peroxodisulfate and 0.46 g sodium acetate. The reaction mixture is heated to 72° C., and then 25 g of freshly distilled vinyl acetate are added dropwise to the solution, after which the water bath is adjusted to 80° C. As soon as the interior temperature has reached 75° C., a further 75 g vinyl acetate are added dropwise, with such a velocity that with moderate reflux the interior temperature lies between 79° and 82° C. Subsequently, another 0.1 g ammonium peroxodisulfate is added in 1/ml distilled water. The reflux very quickly diminishes, and the interior temperature rises to 86° C. The mixture is allowed to polymerize for another 30 minutes at a water bath temperature of 80° C. To remove the residual monomers, the dispersion is mixed with 0.2% by weight of a de-foamer according to Example 7, and the monomers are distilled off under a slight vacuum.

The dispersion blended with the de-foamer according to the present invention showed, in contrast to a dispersion without de-foamer, no excessive foaming during the removal of the monomers under vacuum.

It will be understood that each of the elements described above, or two or more together, may also find a useful application in other types of systems differing from the types described above.

While the invention has been illustrated and described as embodied in a de-foamer and process for its production, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of the present invention.

What is claimed as new and desired to be protected by Letters Patent is set forth in the appended claims:

1. A de-foamer composition produced in situ in an organic carrier medium by a process comprising reacting mono- and/or polyfunctional isocyanates with mono and/or polyfunctional amines at temperatures lying below the melting temperature of the resulting urea in said carrier medium, said organic carrier medium not being a true solvent for said urea, said de-foamer containing as an active component at least one urea of the formula:

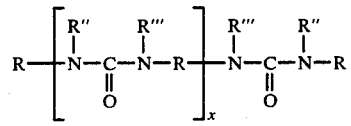

wherein
R is $C_4$ to $C_{30}$ alkyl;
R' is $C_2$ to $C_{12}$ alkylene, phenylene, or naphthylene with or without substitution by one or more $C_1$ to $C_9$ alkyl groups, or cycloalkylene;
R" is H or $CH_3$;
R'" is H or $CH_3$; and
x is 0 or 1,
said reaction being performed at a temperature lying below the melting temperature of the resulting urea whereby the resulting urea is formed in the carrier medium as a monodispersed or micellular structure.

2. A de-foamer according to claim 1, containing as active ingredient a urea of the formula:

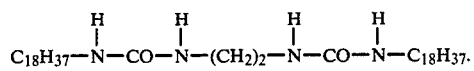

3. A de-foamer according to claim 1, containing as active ingredient a urea of the formula:

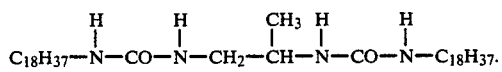

4. A de-foamer according to claim 1, containing as active ingredient a urea of the formula:

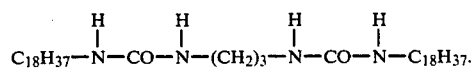

5. A de-foamer according to claim 1, containing as active ingredient a urea of the formula:
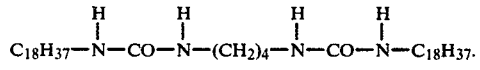
6. A de-foamer according to claim 1, containing as active ingredient a urea of the formula:
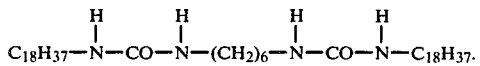
7. A de-foamer according to claim 1, containing as active ingredient a urea of the formula:
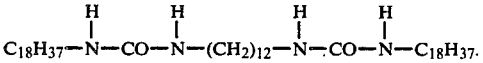
8. A de-foamer according to claim 1, containing as active ingredient a urea where x is 1.
* * * * *